US011647916B2

(12) United States Patent
Sakai et al.

(10) Patent No.: US 11,647,916 B2
(45) Date of Patent: May 16, 2023

(54) BIOLOGICAL INFORMATION DETECTION SYSTEM AND BIOLOGICAL INFORMATION DETECTION METHOD

(71) Applicant: Takahiko Kishi, Kanagawa (JP)

(72) Inventors: Yusuke Sakai, Kanagawa (JP); Takahiko Kishi, Kanagawa (JP)

(73) Assignee: Takahiko Kishi, Kanagawa (JP)

( * ) Notice: Subject to any disclaimer, the term of this patent is extended or adjusted under 35 U.S.C. 154(b) by 258 days.

(21) Appl. No.: 16/604,201

(22) PCT Filed: Jan. 10, 2018

(86) PCT No.: PCT/JP2018/000236
§ 371 (c)(1),
(2) Date: Oct. 10, 2019

(87) PCT Pub. No.: WO2018/189970
PCT Pub. Date: Oct. 18, 2018

(65) Prior Publication Data
US 2020/0029852 A1 Jan. 30, 2020

(30) Foreign Application Priority Data

Apr. 11, 2017 (WO) .................. PCT/JP2017/014754

(51) Int. Cl.
*A61B 5/05* (2021.01)
*A61B 5/00* (2006.01)
(Continued)

(52) U.S. Cl.
CPC .............. *A61B 5/05* (2013.01); *A61B 5/6804* (2013.01); *A61B 5/6892* (2013.01);
(Continued)

(58) Field of Classification Search
None
See application file for complete search history.

(56) References Cited

U.S. PATENT DOCUMENTS

| 4,926,868 A | 5/1990 | Larsen |
| 2003/0117149 A1* | 6/2003 | Conrads ................... G01F 1/66 324/637 |

(Continued)

FOREIGN PATENT DOCUMENTS

| JP | 2013153783 | 8/2013 |
| JP | 2014090877 | 5/2014 |

OTHER PUBLICATIONS

International Search Report and Written Opinion from PCT/JP2018/000236 dated Mar. 20, 2018 along with English translation of the Search Report.

*Primary Examiner* — Yi-Shan Yang
(74) *Attorney, Agent, or Firm* — Calfee, Halter & Griswold LLP

(57) ABSTRACT

In order to stably detect biological information such as the heartbeat, respiration, and pulse waves of a living organism, a biological information detection system that detects biological information comprises: a transmission antenna arranged on one side of the living organism and irradiating radio waves of prescribed polarized waves on to the living organism; a reception antenna arranged on the other side of the living organism and receiving transmitted waves being polarized waves orthogonal to the radio waves of prescribed polarized waves in a step in which same are transmitted through the living organism; and a detection unit that detects biological information on the basis of the transmitted waves received by the reception antenna.

7 Claims, 7 Drawing Sheets

(51) Int. Cl.
*A61B 5/024* (2006.01)
*A61B 5/0507* (2021.01)
*A61B 5/08* (2006.01)

(52) U.S. Cl.
CPC ......... *A61B 5/02444* (2013.01); *A61B 5/0507* (2013.01); *A61B 5/08* (2013.01)

(56) References Cited

U.S. PATENT DOCUMENTS

| | | | |
|---|---|---|---|
| 2005/0143667 A1 | 6/2005 | Park et al. | |
| 2015/0157195 A1* | 6/2015 | Iwaisako | A61B 5/065 600/109 |
| 2015/0164364 A1* | 6/2015 | Kim | A61B 5/0507 600/407 |
| 2017/0042446 A1 | 2/2017 | Park et al. | |
| 2018/0226727 A1* | 8/2018 | Sato | H01Q 13/106 |
| 2019/0380634 A1* | 12/2019 | Yamada | A61B 5/6814 |

\* cited by examiner

| TRANSMITTING ANTENNA | RECEPTION CHARACTERISTIC OF RECEIVING ANTENNA | | | | | | | | | | | |
|---|---|---|---|---|---|---|---|---|---|---|---|---|
| | HORIZONTAL POLARIZATION | | | VERTICAL POLARIZATION | | | RIGHT-HANDED CIRCULAR POLARIZATION | | | LEFT-HANDED CIRCULAR POLARIZATION | | |
| | PASSING WAVE | SURFACE WAVE | DIFFRACTED WAVE | PASSING WAVE | SURFACE WAVE | DIFFRACTED WAVE | PASSING WAVE | SURFACE WAVE | DIFFRACTED WAVE | PASSING WAVE | SURFACE WAVE | DIFFRACTED WAVE |
| HORIZONTAL POLARIZATION | STABLE | STABLE | STABLE | STABLE | NO RECEPTION | NO RECEPTION | UNSTABLE | UNSTABLE | UNSTABLE | UNSTABLE | UNSTABLE | UNSTABLE |
| VERTICAL POLARIZATION | STABLE | NO RECEPTION | NO RECEPTION | STABLE | STABLE | STABLE | UNSTABLE | UNSTABLE | UNSTABLE | UNSTABLE | UNSTABLE | UNSTABLE |
| RIGHT-HANDED CIRCULAR POLARIZATION | UNSTABLE | UNSTABLE | UNSTABLE | UNSTABLE | UNSTABLE | UNSTABLE | STABLE | STABLE | STABLE | STABLE | STABLE | STABLE |
| LEFT-HANDED CIRCULAR POLARIZATION | UNSTABLE | UNSTABLE | UNSTABLE | UNSTABLE | UNSTABLE | UNSTABLE | STABLE | NO RECEPTION | NO RECEPTION | STABLE | STABLE | STABLE |

FIG. 3

BIOLOGICAL INFORMATION DETECTION SYSTEM AND BIOLOGICAL INFORMATION DETECTION METHOD

RELATED APPLICATIONS

The present application is a 35 U.S.C. 371 U.S. national stage application entry of PCT International Application No. PCT/JP2018/000236, filed on Jan. 10, 2018, which claims the benefit of International Patent Application No. PCT/JP2017/014754, filed on Apr. 11, 2017, the entire disclosures of which are incorporated herein by reference.

TECHNICAL FIELD

The present invention relates to a biological information detection system and a biological information detection method for detecting biological information of a living body.

BACKGROUND ART

Conventionally, a technology is developed for non-invasively detecting biological information such as heartbeat by receiving a radio wave such as a microwave radiated on a human body and performing detection based on the received radio wave.

Patent Literature (hereinafter, referred to as PTL) 1, for example, discloses heartbeat detection device that receives a microwave which is radiated to a predetermined part of a measurement subject and which is transmitted through the body of the measurement subject, and performs phase detection or amplitude detection on the received microwave to detect heartbeat of the measurement subject based on the results.

PTL 2 discloses a biological information detection system including an electromagnetic wave oscillating section that irradiates a living body with an electromagnetic wave, and a scattered electromagnetic wave receiving section that receives an electromagnetic wave whose polarization plane is rotated by 90° with respect to the electromagnetic wave radiated from the electromagnetic wave oscillating section when the wave is reflected on the body surface of the living body, and in the biological information detection system, the scattered electromagnetic wave receiving section calculates physiological index of the living body from the received electromagnetic wave.

CITATION LIST

Patent Literature

PTL 1 Japanese Patent Application Laid-Open No. 2013-153783
PTL 2 Japanese Patent Application Laid-Open No. 2014-90877

SUMMARY OF INVENTION

Technical Problem

In the conventional technology of PTL 1, the received microwave includes not only a transmitted wave which is transmitted through the body of the measurement subject but also a diffracted wave which is diffracted outside the body and reaches, and a surface wave which propagates along the surface of the body (hereinafter such a surface wave is referred to as a body surface wave), and as the transmitted wave, diffracted wave, and body surface wave interfere with each other, it may be difficult to detect heartbeat stably in some cases.

Specifically, when a diffracted wave that fluctuates due to body movement but does not include biological information is received, biological information included in a transmitted wave is suppressed according to the intensity of the diffracted wave. Therefore, as the intensity of the diffracted wave increases, the detection of the biological information becomes difficult and only the body movement can be detected.

In addition, the above described body surface wave is subject to fluctuations due to the body movement and breathing which appear greatly on the body surface. For example, when a respiratory wave, a component of the body surface wave, fluctuated due to breathing is received during the detection of heartbeat by using a transmitted wave, not only does the respiratory wave interferes with the transmitted wave, but also the harmonics of the respiratory wave may cause interference with the transmitted wave. The influences of the body movement and respiration increase as the intensity of the body surface wave increases, making the stable detection of the heartbeat difficult.

In addition, in the conventional technology of PTL 2, the scattered electromagnetic wave receiving section receives the reflected wave that is reflected on the body surface of a living body, and thus even though the body movement appearing on the body surface may be detected, it is difficult to detect biological information such as heartbeat. Even though the inside of a body is irradiated with an electromagnetic wave, the intensity of the reflected wave reflected on the body surface is greater than the intensity of the reflected wave reflected inside the body. Further, as the reflected waves interfere with each other, it is difficult to detect biological information from the reflected wave that is reflected inside the body.

An object of the present invention is to provide a biological information detection system and a biological information detection method which can stably sense biological information such as heartbeat, respiration, and a pulse wave.

Solution to Problem

The biological information detection system according to the present invention is for detecting biological information of a living body, and the biological information detection system includes a transmitting antenna that irradiates the living body with a predetermined polarized radio wave, the transmitting antenna being disposed on a first side of the living body; a receiving antenna that receives a transmitted wave which becomes a polarized wave orthogonal to the radio wave during a process of being transmitted through a body of the living body, the receiving antenna being disposed on a second side of the living body; and a detection section that detects biological information based on the transmitted wave received by the receiving antenna.

The biological information detection method according to the present invention is for detecting biological information of a living body, and the biological information detection method includes transmitting from a first side of the living body a predetermined polarized radio wave for irradiating the living body; receiving on a second side of the living body a transmitted wave which becomes a polarized wave orthogonal to the radio wave during a process of being transmitted through a body of the living body; and detecting biological information based on the transmitted wave received in the receiving.

Advantageous Effects of Invention

The present invention is capable of stably sensing biological information such as heartbeat, respiration, and a pulse wave.

BRIEF DESCRIPTION OF DRAWINGS

FIG. 3 describes reception condition of a microwave emitted from a transmitting antenna at a receiving antenna;

DESCRIPTION OF EMBODIMENT

Hereinafter, embodiments of the present invention will be described in detail with reference to the drawings.

Hereinafter, a case where a living body whose biological information is detected by a biological information detection system is a person and the detected biological information is heartbeat will be described. However, the present invention is not limited to this case, and can be widely applied to living bodies other than people and to detection of other types of biological information such as a pulse wave and respiration.

Herein, heartbeat is a pulse of heart. A pulse wave is a waveform that indicates changes in blood vessel volume and blood pressure that occur accompanying the heartbeat. The detection of heartbeat detects the pulse of heart, and the detection of the pulse wave detects changes in blood vessel volume and blood pressure.

Figure 1:
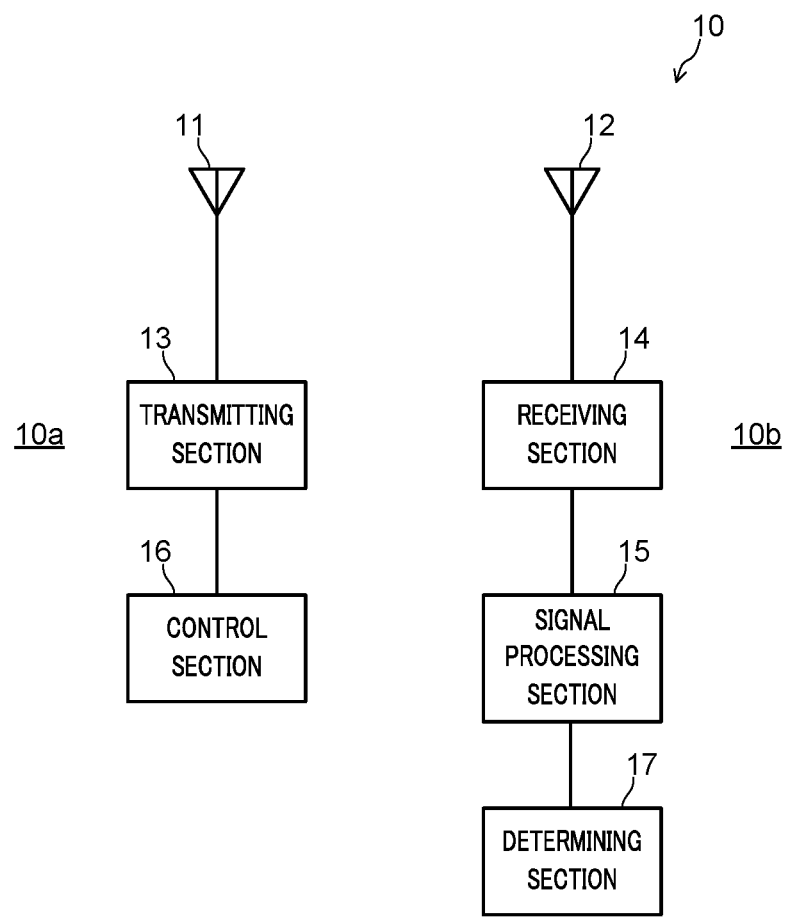
FIG. 1 illustrates an example of a configuration of a biological information detection system according to the present embodiment.

FIG. 1 illustrates an example of a configuration of biological information detection system 10 according to the present embodiment. As illustrated in FIG. 1, this biological information detection system 10 includes transmitting device 10a including transmitting antenna 11, transmitting section 13 and control section 16, and receiving device 10b including receiving antenna 12, receiving section 14, signal processing section 15 and determining section 17.

Transmitting antenna 11 irradiates a person with a microwave with a predetermined polarization. The predetermined polarization is, for example, right-handed circular polarization or left-handed circular polarization. The predetermined polarization may be linear polarization such as horizontal polarization. Herein, the radio wave emitted from transmitting antenna 11 is a microwave, but any radio wave may be used, such as a radio wave having another wavelength.

Hereinafter, for easier understanding of the explanation for the propagation direction of the microwave and the like, an orthogonal coordinate system in a three-dimensional space consisting of x-axis, y-axis, and z-axis orthogonal to each other is used. The direction in which transmitting antenna 11 emits the microwave most strongly is set to be the positive direction of z-axis.

Transmitting antenna 11 is, for example, a planar antenna such as a microstrip antenna. When a planar antenna is used as transmitting antenna 11, transmitting antenna 11 has the maximum emission intensity in the direction perpendicular to a substrate surface.

In particular, transmitting antenna 11 is preferably a thin planar antenna for installing transmitting antenna 11 adjacent to a person. This is because transmitting antenna 11 can be easily installed in a place with a limited installation space, such as the backrest of a chair when the substrate surface of transmitting antenna 11 is provided parallel to the person.

Transmitting antenna 11 includes a radio wave emission prevention structure that prevents emission of radio waves in the negative direction of z-axis (the direction opposite to the direction in which a microwave is emitted) and in the x- or y-axis direction.

The radio wave emission prevention structure is, for example, an electromagnetic band gap (EBG) structure. The EBG structure includes therein periodically arranged unit structures which are smaller than the wavelength of a radio wave. In the EBG structure, for example, rectangular metal electrodes are periodically arranged on the surface of a dielectric substrate, and a metal film is formed on the back side of the dielectric substrate, where the metal electrodes and the metal film are connected by short-circuit pins. Such a structure is known as a mushroom structure EBG.

An EBG having such a structure has a characteristic such that the propagation of a radio wave in a specific frequency band is suppressed on the surface of the EBG. Therefore, when an EBG structure having the same resonance frequency as that of transmitting antenna 11 is disposed around transmitting antenna 11, the EBG structure can attenuate microwaves emitted in the x- or y-axis direction.

The EBG structure can also suppress the emission of a microwave, which is propagated on the surface and diffracted at the edge of the structure, in the negative direction of z-axis. Transmitting antenna 11 according to the embodiments of the present invention thus has improved directivity compared to conventional antennas.

When transmitting antenna 11 emits a circularly polarized microwave, the axial ratio of the circularly polarized wave becomes the best in the positive direction of z axis, and degrades toward the x- or y-axis direction. The EBG structure can attenuate the circularly polarized microwave in a region where the axial ratio is degraded. Transmitting antenna 11 thus can efficiently transmit a microwave with desired polarization toward receiving antenna 12.

The EBG structure may be disposed at any position relative to transmitting antenna 11 as long as the emission of a microwave emitted from transmitting antenna 11 can be attenuated in the x- and y-axis directions and the negative direction of z-axis.

As transmitting antenna 11, any antenna other than the microstrip antenna may also be used. For example, a helical antenna may be used as transmitting antenna 11. The helical antenna as transmitting antenna 11 can transmit a microwave with an excellent axial ratio.

Transmitting section 13 is a device that transmits a microwave via transmitting antenna 11. Control section 16 is a device that controls transmitting section 13 for transmitting a microwave. Control section 16 performs, for example, setting of the frequency of a microwave to be transmitted by transmitting section 13. Providing control section 16 is not essential, and transmitting section 13 may transmit a previously defined microwave.

Receiving antenna 12 receives a microwave with a polarization (hereinafter also referred to as "polarized wave") which becomes orthogonal to the above-described microwave due to reflection in the human body. For example, when the predetermined polarization is right-handed circular polarization, receiving antenna 12 receives a microwave with left-handed circular polarization (hereinafter also referred to as "left-handed circularly polarized microwave") that is orthogonal to the microwave with the right-handed circular polarization (hereinafter also referred to as "right-handed circularly polarized microwave").

Receiving antenna 12 is, for example, a planar antenna such as a microstrip antenna.

In particular, receiving antenna 12 is preferably a thin planar antenna when receiving antenna 12 is installed close to a person. This is because receiving antenna 12 can be easily installed in a place with a limited installation space when the substrate surface of receiving antenna 12 is provided parallel to the person.

As with transmitting antenna 11, receiving antenna 12 includes the above-described radio wave emission prevention structure. Receiving antenna 12 thus has improved directivity compared to conventional antennas.

In addition, when receiving antenna 12 receives a circularly polarized microwave, the radio wave emission prevention structure of receiving antenna 12 can suppress the reception of a microwave with undesired polarization in a region where the axial ratio is degraded. Therefore, receiving antenna 12 can efficiently receive a microwave with desired polarization.

Receiving antenna 12 may also be any antenna other than the microstrip antenna.

Receiving section 14 is a device that receives a microwave via receiving antenna 12. Receiving section 14 performs, for example, setting of the frequency of a microwave to be received by receiving antenna 12. A control section may be provided in receiving device 10b for performing, for example, setting of the frequency of a microwave to be received by receiving section 14.

Signal processing section 15 is a detection section that detects the heartbeat of a person by performing extraction processing of the heartbeat information from an analog waveform of a microwave received by receiving section 14. A technique for detecting heartbeat by irradiating a person with a microwave is well known, and thus the detailed description thereof is omitted herein.

Determining section 17 is a processing section that performs various types of determination based on the heartbeat detected by signal processing section 15. Determining section 17 determines, for example, whether the heart rate exceeds or falls below a predetermined threshold value.

Figure 2:
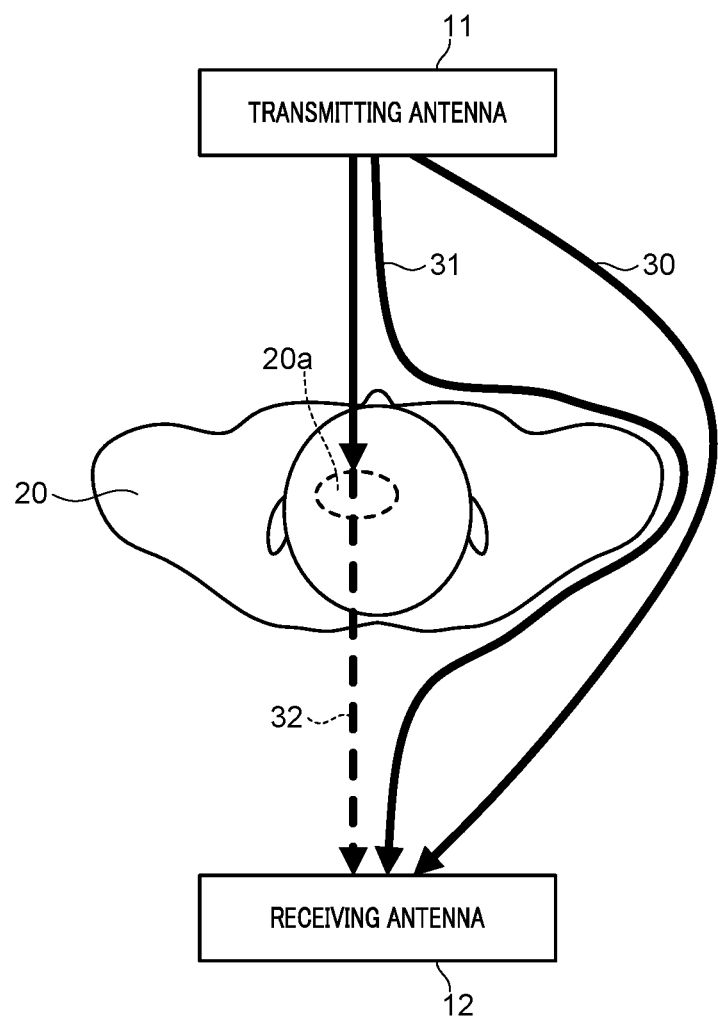
FIG. 2 schematically describes biological information detection in the present invention.

In the following, the biological information detection in the present invention will be schematically described with reference to FIG. 2. FIG. 2 schematically describes biological information detection in the present invention.

Transmitting antenna 11 is disposed on one side of person 20. The one side is, for example, the front side of person 20. Receiving antenna 12 is disposed on the other side of person 20. The other side is, for example, the back side of person 20. Receiving antenna 12 is thus provided at a position facing transmitting antenna 11 with person 20 therebetween.

As illustrated in FIG. 2, main microwaves reaching receiving antenna 12 are diffracted wave 30 that propagates around outside the body of person 20 to reach the opposite side, body surface wave 31 that propagates on the surface of the body of person 20, and transmitted wave 32 that is transmitted through the body of person 20.

For example, when person 20 is irradiated with a right-handed circularly polarized microwave, reflection occurs at the boundary surface of organ 20a having a different dielectric constant in the body of person 20. Transmitted wave 32 having been transmitted through the inside of organ 20a tends to become a left-handed circularly polarized wave orthogonal to the microwave emitted from transmitting antenna 11 due to the reflection in the body.

Meanwhile, diffracted wave 30 and body surface wave 31 do not become a left-handed circularly polarized wave orthogonal to the right-handed circularly polarized microwave emitted from transmitting antenna 11. The right-handed circularly polarized microwave emitted from transmitting antenna 11 may be converted to a left-handed circularly-polarized wave orthogonal to the emitted microwave, by being reflected on the surroundings of the living body, but frequency and intensity thereof depend on the situation of the surrounding installation. In addition, the signal level is lowered due to the reflection in the surroundings.

In general, for receiving a microwave with a predetermined polarization, an antenna that receives a microwave with the same polarization is used. However, in the present invention, by using receiving antenna 12 that receives a polarized microwave orthogonal to a microwave emitted from transmitting antenna 11, it becomes possible to selectively receive transmitted wave 32 that reflects biological information while suppressing the reception of diffracted wave 30 and body surface wave 31.

As a result, it becomes possible to prevent diffracted wave 30 or body surface wave 31 and transmitted wave 32 from interfering with each other, and to stably sense biological information such as heartbeat, respiration, and a pulse wave.

In addition, as transmitting antenna 11 has improved directivity compared to conventional antennas due to the EBG structure as described above, generation of diffracted wave 30 and body surface wave 31 can be reduced. Receiving antenna 12 thus can stably receive transmitting wave 32 having been transmitted through the body of person 20.

In other words, transmitting antenna 11 can increase the intensity of transmitted wave 32 with respect to diffracted wave 30 and body surface wave 31. Signal processing section 15 thus can stably extract biological information from an analog signal received by receiving section 14.

The intensity of diffracted wave 30 and body surface wave 31 becomes small relative to transmitted wave 32, and thus even when diffracted wave 30 and body surface wave 31 become polarized waves orthogonal to the microwave emitted from transmitting antenna 11, the influence of those waves on transmitted wave 32 can be reduced.

In addition, as receiving antenna 12 has improved directivity compared to conventional antennas as described above, reception of diffracted wave 30 and body surface wave 31 can be suppressed. Receiving antenna 12 thus can stably receive transmitted wave 32 having been transmitted through the body of person 20.

Biological information detection system 10 of the present invention increases the intensity of transmitted wave 32 (D/U ratio) with respect to the intensity of diffracted wave 30 and body surface wave 31 that do not include biological information, and thus can stably detect the biological information.

In the above described embodiment, transmitting antenna 11 is disposed on the front side of person 20, and receiving antenna 12 is disposed on the back side of person 20, but the configuration is not limited thereto. For example, transmitting antenna 11 may be disposed on the back side of person 20, and receiving antenna 12 may be disposed on the front side of person 20.

Biological information detection system 10 of the present invention may use extremely low power radio waves that conform to the extremely low power radio standards of the radio law, or the like.

In biological information detection system 10, for example, when using a radio wave that cannot be handled as a weak radio wave under the radio law, a specific license is required, and thus costs are necessary for obtaining such a license.

Even when using a specified low-power radio that does not require such a specified license, it is necessary to obtain a technical standards conformity certification. In this case, it is necessary to implement a wireless communication function or the like in the system, and costs for adding the function are further needed.

Therefore, using a weak radio wave that conforms to the weak radio standards of the radio law can prevent the increase of those costs.

In general, however, when transmitting antenna 11 emits a weak radio wave, it becomes difficult for receiving antenna 12 to receive the radio wave emitted from transmitting antenna 11 with high accuracy. The influence of noise on the radio wave received by receiving antenna 12 also increases.

In the present invention, therefore, when transmitting antenna 11 emits a weak radio wave, for example, an antenna having high gain and sharp directivity, such as a planar helical antenna is used as receiving antenna 12. A sharper directivity can be obtained for the planar helical antenna by increasing the number of turns.

In addition, when transmitting antenna 11 emits a weak radio wave, transmitting antenna 11 is preferably disposed in contact with person 20 or as close to person 20 as possible. Such a configuration enables the reduction of generation of diffracted wave 30 or body surface wave 31. Receiving antenna 12 thus can stably receive transmitted wave 32 having been transmitted through the body of person 20.

When a weak radio wave is used as the radio wave to be emitted from transmitting antenna 11, a secondary effect such that the exposure amount of the radio wave to person 20 can be reduced is brought about for biological information detection system 10.

Biological information detection system 10 of the present invention can be used, for example, for detecting an abnormality of a driver during the driving of a vehicle. For example, installing transmitting antenna 11 at the instrument panel portion of the vehicle and receiving antenna 12 on or in (herein after also referred to as "on/in") the backrest of the seating seat of the driver's seat enables sequential detection of the biological information of the driver during the driving.

In this case, a planar helical antenna having directivity in a direction parallel to a substrate surface of the antenna is employed as transmitting antenna 11, and the planar helical antenna is disposed so that the substrate surface becomes perpendicular to person 20. Such a configuration enables transmitting antenna 11 to be installed discreetly on/in the instrument panel portion.

In addition, when a planar antenna having directivity in a direction perpendicular to the substrate surface is employed as receiving antenna 12 with the substrate surface parallel to person 20, receiving antenna 12 can be easily housed on/in the backrest of the seating seat.

Biological information detection system 10 of the present invention may also be applied to the detection of biological information of person 20 during the operation of a personal computer (PC). For example, installing transmitting antenna 11 in front of a keyboard and receiving antenna 12 on/in the backrest of a chair enables sequential detection of the biological information of person 20 during the operation of the PC.

In this case, when transmitting antenna 11 is thick, it may be difficult to install transmitting antenna 11 due to a limited installation space, or person 20 may feel uncomfortable with the design of the keyboard. Therefore, in such a case, a planar antenna such as a planar helical antenna is employed as transmitting antenna 11. The directivity of transmitting antenna 11 is set to be in the direction of one end face of the antenna.

In addition, when a planar antenna having directivity in a direction perpendicular to the substrate surface is employed as receiving antenna 12 with the substrate surface parallel to person 20, receiving antenna 12 can be easily housed on/in the backrest of the chair.

FIG. 3 describes reception conditions of a microwave emitted from transmitting antenna 11 at receiving antenna 12. In FIG. 3, "stable" indicates that the reception condition of the microwave at receiving antenna 12 is stable. "Unstable" indicates that the reception condition of the microwave at receiving antenna 12 is unstable. "No reception" indicates that the reception of microwaves at receiving antenna 12 is impossible, that is, receiving antenna 12 does not receive microwaves.

When transmitting antenna 11 radiates a horizontally polarized microwave and receiving antenna 12 has a characteristic of receiving a horizontally polarized microwave, the reception conditions of transmitted wave 32, surface wave 21 and diffracted wave 30 at receiving antenna 12 are stable.

When transmitting antenna 11 radiates a horizontally polarized microwave and receiving antenna 12 has a characteristic of receiving a vertically polarized microwave, the reception condition of transmitted wave 32 at receiving antenna 12 is stable. Meanwhile, receiving antenna 12 does not receive surface wave 21 or diffracted wave 30.

When transmitting antenna 11 radiates a horizontally polarized microwave and receiving antenna 12 has a characteristic of receiving a right-handed circularly polarized microwave, the reception conditions of transmitted wave 32, surface wave 21 and diffracted wave 30 at receiving antenna 12 are unstable.

When transmitting antenna 11 radiates a horizontally polarized microwave and receiving antenna 12 has a characteristic of receiving a left-handed circularly polarized microwave, the reception conditions of transmitted wave 32, surface wave 21 and diffracted wave 30 at receiving antenna 12 are unstable.

Accordingly, FIG. 3 shows that when transmitting antenna 11 radiates a horizontally polarized microwave, using receiving antenna 12 with the characteristic of receiving a vertically polarized microwave enables stable reception of only transmitted wave 32.

Similarly, FIG. 3 shows that when transmitting antenna 11 radiates a vertically polarized microwave, using receiving antenna 12 with the characteristic of receiving a horizontally polarized microwave enables stable reception of only transmitted wave 32.

Similarly, FIG. 3 shows that when transmitting antenna 11 radiates a right-handed circularly polarized microwave, using receiving antenna 12 with the characteristic of receiving a left-handed circularly polarized microwave enables stable reception of only transmitted wave 32.

Similarly, FIG. 3 shows that when transmitting antenna 11 radiates a left-handed circularly polarized microwave, using receiving antenna 12 with the characteristic of receiving a right-handed circularly polarized microwave enables stable reception of only transmitted wave 32.

In other words, FIG. 3 shows that a polarized microwave radiated from transmitting antenna 11 toward person 20 becomes a polarized wave having a component orthogonal to the radiated microwave in the body of person 20.

As described above, it is considered that when the reflection or diffraction of the microwave is repeated at the boundary surface of organ 20a having a different dielectric constant in the body, the reflected or diffracted microwave becomes a polarized wave having a component orthogonal to a predetermined polarized wave having entered the body.

Based on such findings, an antenna that receives a polarized microwave orthogonal to a microwave radiated toward person 20 is used as receiving antenna 12 in the present invention.

Biological information detection system 10 illustrated in FIG. 1 may further include at least one of first polarizing filter 40 and second polarizing filter 41.

Figure 4:
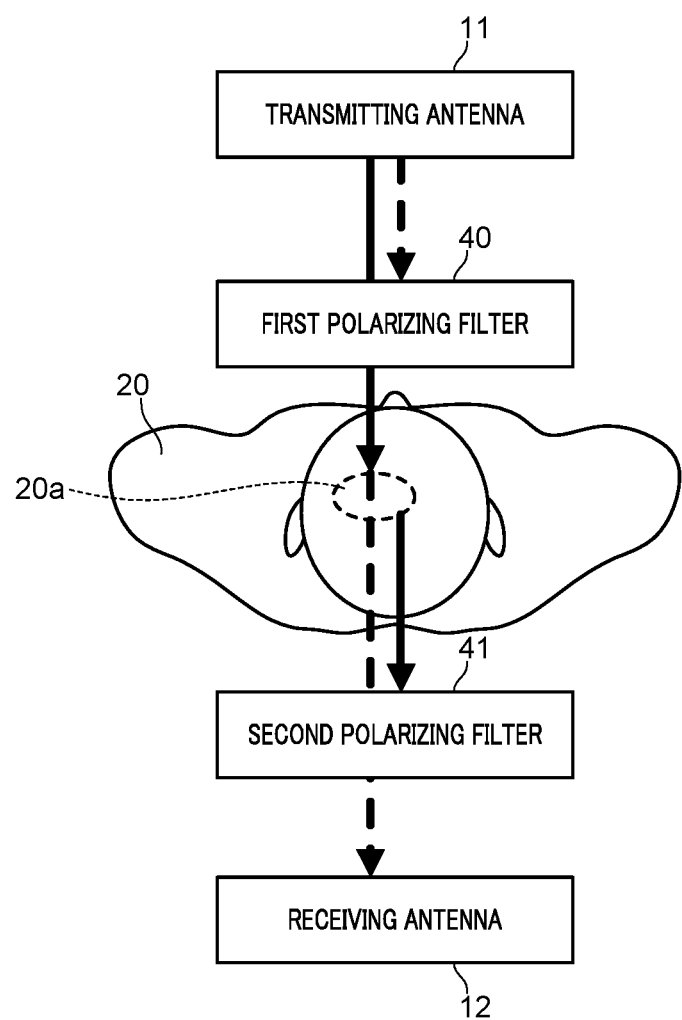
FIG. 4 describes a first polarizing filter and a second polarizing filter.

FIG. 4 describes first polarizing filter 40 and second polarizing filter 41.

As illustrated in FIG. 4, when transmitting antenna 11 is not provided in the vicinity of person 20, first polarizing filter 40 is disposed between transmitting antenna 11 and person 20, and removes microwaves other than the horizontally polarized microwave transmitted by transmitting antenna 11.

Providing first polarizing filter 40 enables prevention of radiation of microwaves other than the horizontally polarized microwave to the inside of a living body. As a result, it becomes possible to prevent the polarization state of transmitted wave 32 received by receiving antenna 12 from becoming unstable, and to realize stable detection of biological information such as heartbeat.

When receiving antenna 12 is not provided in the vicinity of person 20, second polarizing filter 41 is disposed between person 20 and receiving antenna 12, and removes microwaves other than transmitted wave 32 which becomes a polarized wave orthogonal to the horizontally polarized microwave transmitted by transmitting antenna 11 due to the reflection in the body of person 20.

When receiving antenna 12 is installed away from person 20, transmitted wave 32 that did not become a polarized wave orthogonal to the horizontally polarized microwave when being transmitted through the body of person 20, diffracted wave 30, or body surface wave 31 may become a polarized wave orthogonal to the horizontally polarized microwave due to the influence of an object between person 20 and receiving antenna 12.

In this case, interference occurs between transmitted wave 32 which becomes a polarized wave orthogonal to the horizontally polarized microwave due to the reflection in the body of person 20, and transmitted wave 32, diffracted wave 30 and body surface wave 31 which become polarized waves orthogonal to the horizontally polarized microwave due to the influence of the object between person 20 and receiving antenna 12, and thus the reception condition may become unstable.

Second polarizing filter 41 is thus provided to remove microwaves other than transmitted wave 32 that is a polarized wave orthogonal to the horizontally polarized microwave in the vicinity of person 20, and to allow only transmitted wave 32 with a desired polarization to pass therethrough.

With this configuration, it becomes possible to prevent the polarization state of transmitted wave 32 received by receiving antenna 12 from becoming unstable except for the case where a microwave transmitted by transmitting antenna 11 is, for example, reflected between person 20 and receiving antenna 12 a plurality of times, thereby becoming a polarized wave orthogonal to the horizontally polarized microwave. Therefore, using transmitted wave 32 which becomes a polarized wave orthogonal to the horizontally polarized microwave due to the reflection in the body of person 20 realizes stable detection of biological information such as heartbeat.

One of the reasons why transmitting antenna 11 or receiving antenna 12 is installed away from person 20 is that when transmitting antenna 11 and receiving antenna 12 are provided at positions close to a human body, the characteristics of transmitting antenna 11 and receiving antenna 12 change.

Even when transmitting antenna 11 or receiving antenna 12 is installed away from person 20, biological information detection system 10 according to the present embodiment can realize stable detection of biological information by providing first polarizing filter 40 or second polarizing filter 41.

As a result, the degree of freedom of disposition of transmitting antenna 11 and receiving antenna 12 can be increased.

At least one of first polarizing filter 40 and second polarizing filter 41 may be provided on/in clothes such as an apron worn by person 20.

Figure 5:
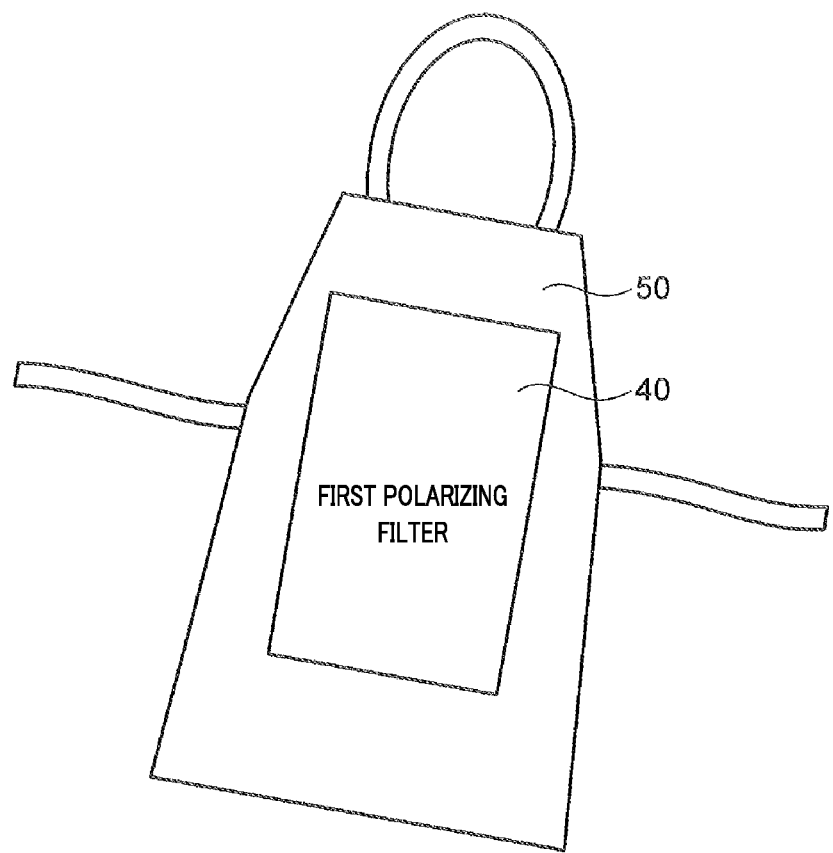
FIG. 5 illustrates an apron provided with the first polarizing filter.

FIG. 5 illustrates apron 50 provided with first polarizing filter 40. When person 20 wears apron 50 illustrated in FIG. 5 and faces in a direction where transmitting antenna 11 is present, microwaves other than the horizontally polarized microwave transmitted by transmitting antenna 11 can be removed while the microwave emitted from transmitting antenna 11 is transmitted through the body of person 20 via first polarizing filter 40.

Second polarizing filter 41 may be provided on the back side of the clothes worn by person 20. This configuration enables removal of microwaves other than the vertically polarized microwave orthogonal to the horizontally polarized microwave transmitted by transmitting antenna 11.

First polarizing filter 40 may be provided on the abdomen side of the clothes worn by person 20 and second polarizing filter 41 may be provided on the back side thereof This configuration can easily dispose first polarizing filter 40 and second polarizing filter 41 in a state where their functions are performed.

In addition, at least one of first polarizing filter 40 and second polarizing filter 41 may be provided on/in an apparatus such as a chair or bed supporting person 20.

Figure 6:
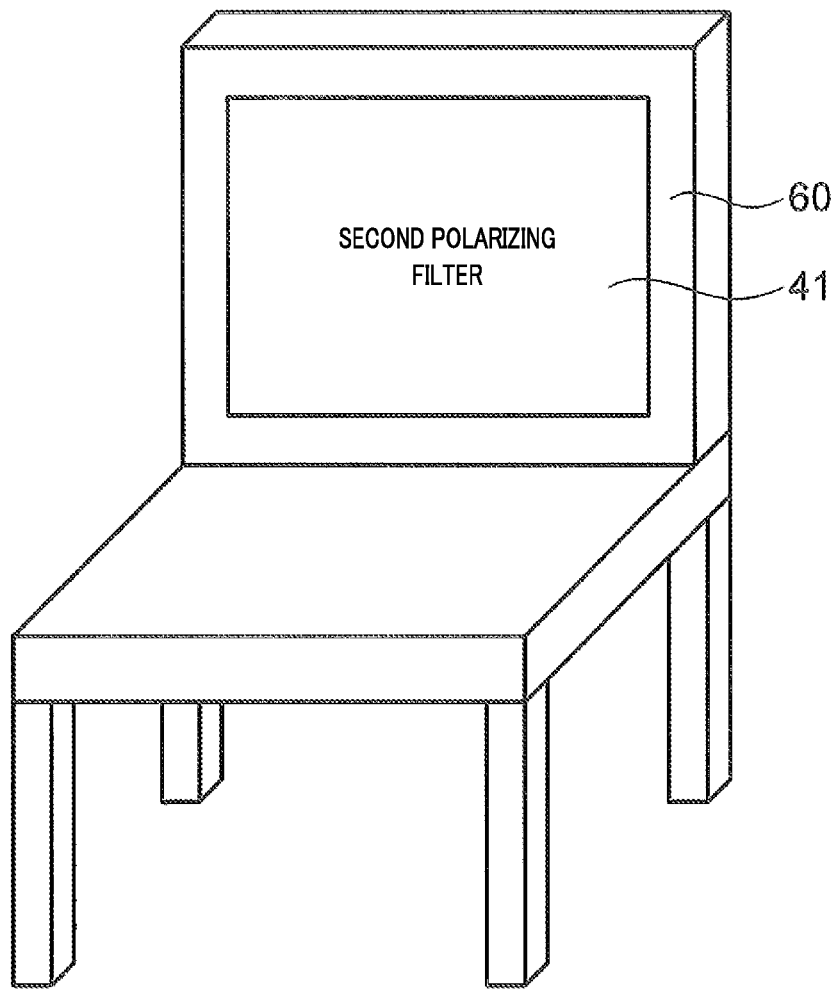
FIG. 6 illustrates an example of a chair provided with the second polarizing filter.

FIG. 6 illustrates an example of chair 60 provided with second polarizing filter 41. When person 20 sits on chair 60 illustrated in FIG. 6, a microwave emitted from transmitting antenna 11 and having been transmitted through the body of person 20 passes through second polarizing filter 41. As a result, stable detection of biological information can be realized in a state where person 20 sits on chair 60.

Figure 7:
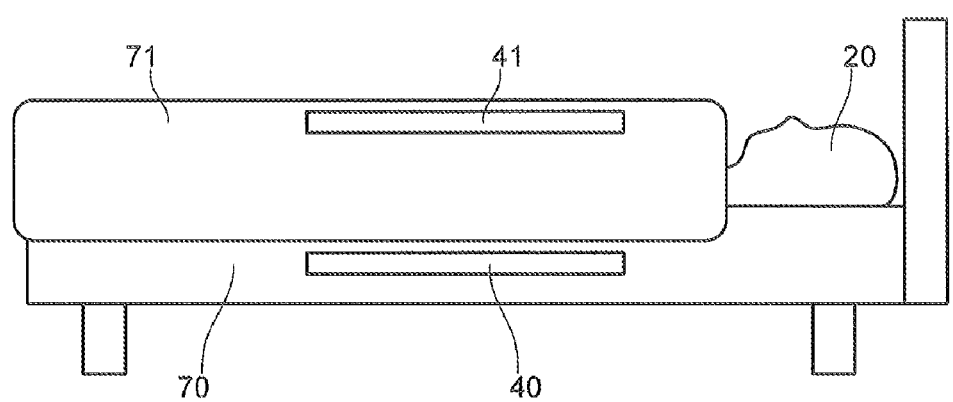
FIG. 7 illustrates an example of a bed provided with the first polarizing filter and a coverlet provided with the second polarizing filter.

FIG. 7 illustrates an example of bed 70 provided with first polarizing filter 40 and coverlet 71 provided with second polarizing filter 41.

Although not shown in FIG. 7, in this case, transmitting antenna 11 is provided below bed 70 (for example, the floor), and receiving antenna 12 is provided above coverlet 71 (for example, the ceiling of the room).

This configuration can also easily dispose first polarizing filter 40 and second polarizing filter 41 in a state where their functions are performed. In particular, with the configuration of FIG. 7, the biological information of person 20 can be easily detected even when person 20 is bedridden.

Alternatively, biological information of person 20 can be detected by providing first polarizing filter 40 on/in coverlet 71, second polarizing filter 41 on/in bed 70, transmitting antenna 11 above coverlet 71, and receiving antenna 12 below bed 70.

The entire contents of the specification, drawings and abstract included in the international application of PCT/JP2017/014754 filed on Apr. 11, 2017 is incorporated herein by reference.

INDUSTRIAL APPLICABILITY

The present invention is suitable for use in a biological information detection system for detecting biological information of a living body.

REFERENCE SIGNS LIST

10 Biological information detection system
10a Transmitting device
10b Receiving device
11 Transmitting antenna
12 Receiving antenna
13 Transmitting section
14 Receiving section
15 Signal processing section
16 Control section
17 Determining section
20 Person
20a Organ
30 Diffracted wave
31 Body surface wave
32 Transmitted wave
40 First polarizing filter
41 Second polarizing filter
50 Apron
60 Chair
70 Bed
71 Coverlet

The invention claimed is:

1. A biological information detection system for detecting biological information of a living body, comprising:
  a transmitting antenna that irradiates the living body with a predetermined polarized radio wave, the transmitting antenna being disposed on a first side of the living body; and
  a receiving antenna that receives a transmitted wave that is a polarized wave orthogonal to the predetermined polarized radio wave and that results from a portion of the predetermined polarized radio wave that has transmitted through a body of the living body, the receiving antenna being disposed on a second side of the living body, wherein:
  the receiving antenna selectively receives the transmitted wave while suppressing reception of another portion of the predetermined polarized radio wave that has not transmitted through the body; and
  the biological information is detected by extraction processing of the biological information from the transmitted wave received by the receiving antenna.

2. The biological information detection system according to claim 1, wherein:
  at least one of the transmitting antenna and the receiving antenna includes an Electromagnetic Band Gap (EBG) structure.

3. The biological information detection system according to claim 1, further comprising:
  at least one of a first polarizing filter that removes radio waves other than the predetermined polarized radio wave and a second polarizing filter that removes radio waves other than the transmitted wave, the first polarizing filter being disposed between the transmitting antenna and the living body, the second polarizing filter being disposed between the living body and the receiving antenna.

4. The biological information detection system according to claim 3, wherein:
  at least one of the first polarizing filter and the second polarizing filter is provided in an apparatus supporting the living body.

5. The biological information detection system according to claim 3, wherein:
  at least one of the first polarizing filter and the second polarizing filter is provided in clothes worn by the living body or bedclothes used by the living body.

6. The biological information detection system according to claim 1, further comprising:
  at least one of a first polarizing filter that removes radio waves other than the predetermined polarized radio wave and a second polarizing filter that removes radio waves other than the transmitted wave, the first polarizing filter being disposed in the vicinity of the living body and between the transmitting antenna and the living body such that the first polarizing filter is arranged apart from the transmitting antenna, the second polarizing filter being disposed in the vicinity of the living body and between the receiving antenna and the living body such that the second polarizing filter is arranged apart from the receiving antenna.

7. A biological information detection method for detecting biological information of a living body, comprising:
  transmitting, from a first side of the living body, a predetermined polarized radio wave for irradiating the living body;
  receiving, on a second side of the living body, a transmitted wave that which is a polarized wave orthogonal to the predetermined polarized radio wave and that results from a portion of the predetermined polarized radio wave that has transmitted through a body of the living body; and
  detecting the biological information based on the transmitted wave received in the receiving, wherein:
  the transmitted wave is selectively received while reception of another portion of the predetermined polarized radio wave that has not transmitted through the body is suppressed.

* * * * *